| United States Patent [19] | [11] | 4,239,770 |
|---|---|---|
| Kyburz et al. | [45] | Dec. 16, 1980 |

[54] SUBSTITUTED 2-PYRROLIDINONES FOR COUNTERACTING CEREBRAL INSUFFICIENCY

[75] Inventors: Emilio Kyburz, Reinach; Werner Aschwanden, Ettingen, both of Switzerland

[73] Assignee: Hoffmann-La Roche Inc., Nutley, N.J.

[21] Appl. No.: 8,674

[22] Filed: Feb. 2, 1979

[30] Foreign Application Priority Data

Feb. 10, 1978 [CH] Switzerland ................ 1404/78

[51] Int. Cl.³ ............................................ A61K 31/40
[52] U.S. Cl. ............................................ 424/274
[58] Field of Search ................................ 424/274

[56] References Cited

U.S. PATENT DOCUMENTS 2,915,430  12/1959  Taber .................... 424/274

FOREIGN PATENT DOCUMENTS 436304  5/1967  Switzerland .

OTHER PUBLICATIONS

Chem. Abst. 63-16256e, (1965).

*Primary Examiner*—Stanley J. Friedman
*Attorney, Agent, or Firm*—Jon S. Saxe; George M. Gould; Peter R. Shearer

[57] ABSTRACT

1-Substituted 2-pyrrolidinones and pharmaceutical compositions containing same are described. The pharmaceutical compositions are useful in counteracting cerebral insufficiency or improving intellectual capacity.

2 Claims, No Drawings

SUBSTITUTED 2-PYRROLIDINONES FOR COUNTERACTING CEREBRAL INSUFFICIENCY

BRIEF SUMMARY OF THE INVENTION

This invention relates to pharmaceutical compositions capable of counteracting cerebral insufficiency or improving intellectual capacity comprising at least one compound of the formula

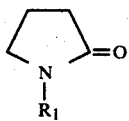

wherein $R_1$ is o-methoxybenzoyl, m-methoxybenzyl, p-methoxybenzyl or p-fluorobenzyl and a pharmaceutically acceptable inert carrier material.

In another aspect, the invention relates to a method of use of the compounds of formula 1 as agents in counteracting cerebral insufficiency or improving intellectual capacity.

DETAILED DESCRIPTION OF THE INVENTION

The invention relates to pharmaceutical compositions capable of counteracting cerebral insufficiency or improving intellectual capacity comprising at least one compound of the formula

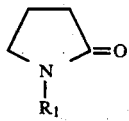

wherein $R_1$ is o-methoxybenzoyl, m-methoxybenzyl, p-methoxybenzyl or p-fluorobenzyl and a pharmaceutically acceptable inert carrier material. The preferred compound of formula I is 1-(p-methoxybenzyl)-2-pyrrolidinone. The compounds of formula I are known in the art, as are suitable methods for their preparation, see Chemical Abstracts 63, 16256 e (1965) and German Offenlegungsschrift No. 2556457.

The invention is based on the discovery that compounds of formula I are useful in the control or prevention of cerebral insufficiency or in the improvement of intellectual capacity. Therefore, the compounds are useful as agents for the treatment of cerebral insufficiency and improvement of intellectual capacity, for example, in cases of cerebral seizure, in geriatry, in alcoholism, etc.

The ability of the compounds of formula I to counteract experimentally produced cerebral insufficiency in mammals was determined by means of test procedures which are described hereinafter:

POSTHYPERCAPNIC "AVOIDANCE" ACQUISITION

The test apparatus is a "shuttle box" having a 10 cm high hurdle in the middle and an electrifiable grid floor. A "loudspeaker" is mounted in the soundproof chamber. One group of untrained rats (120–150 g.) is injected with a test preparation and a second group is injected with a control preparation. One or three hours after administration, each group is placed in a pure carbon dioxide environment for 12 seconds. A third group of 10 rats is treated neither with the test preparation nor with carbon dioxide. Three minutes after treatment with carbon dioxide the rats of all three groups must learn an escape response and an avoidance response in the "shuttle box" in the following sequence: 10 seconds silence-5 seconds noise ("avoidance response")-15 seconds noise+foot-shock ("escape response"). The sequence is repeated six times. For each of the six experiments the reaction time (time until the rat jumps over the hurdle) of each rat is measured and the statistical significance of the differences between the mean group reaction times is calculated by means of the Mann-Whitney U-test.

An "active dosage" of a test preparation is a dosage which shows significant activity during the six experiments. Significant activity is exhibited when the mean reaction times of the animals treated with the test preparation and carbon dioxide are significantly better than those of the animals treated only with carbon dioxide and about equal to those of the animals treated neither with the test preparation nor with carbon dioxide.

In the aforedescribed test, the compounds of formula I exhibited a significant activity at the following dosages:

| $R_1$ | Minimum active dosage |
| --- | --- |
| p-Methoxybenzyl | 10 mg/kg i.p. (after 1 hour) |
|  | 50 mg/kg p.o. (after 1 hour) |
| p-Fluorobenzyl | 50 mg/kg i.p. (after 1 hour) |
|  | 300 mg/kg p.o. (after 1 hour) |
| o-Methoxybenzoyl | 30 mg/kg i.p. (after 1 hour) |
|  | 100 mg/kg p.o. (after 1 hour) |
| m-Methoxybenzyl | 50 mg/kg i.p. (after 3 hours) |

"PASSIVE AVOIDANCE" TEST WITH ELECTROSHOCK AMNESIA

The test apparatus is a Skinner box having an electrifiable grid floor with a grey quadrangular platform in one corner. Untrained male rats weighing 100–200 g are placed on the platform. When the rats climb down onto the grid floor they receive an electric shock. After 3–5 experiments, the rats exhibit a "passive avoidance response", that is, refusal to climb down from the platform. Immediately after acquisition of the passive avoidance response three groups of 20 rats each are formed. One group receives an electric shock between the ears and i.p. injection of the test preparation. The second group receives an electric shock between the ears and an i.p. injection of sodium chloride. The third group receives only an i.p. injection of sodium chloride. After three hours, each rat is placed on the platform once and the retention time, that is, the time the rat remains on the platform (maximum 60 seconds), is measured. The significant activity of the test preparation in comparison to the two control groups is calculated by means of the Rang Test.

An "active" dosage of a test preparation is a dosage which exhibits a significant protective activity against the electric shock. In other words the animals treated with an active dosage of a test preparation and electric shock exhibit a retention time about equal to that of the animals not treated with electric shock, whereas the animals treated with sodium chloride and electric shock exhibit a relatively short retention time.

In this test the minimum active dosage of 1-(p-methoxybenzyl)-2-pyrrolidinone was 50 mg/kg i.p.

INHIBITION OF HALOPERIDOL-INDUCED "KNOCK OUT" IN A "CONTINUOUS AVOIDANCE" TEST SEQUENCE

Male, untrained squirrel monkeys (Saimiri sciureus), each weighing 0.6 to 1.2 kg, are trained in a two-lever Skinner box in the following "continuous avoidance" sequence: "avoidance-shock"-interval 40 seconds; "shock-shock"-interval 20 seconds; foot-shock-maximum 5 seconds. Monkeys having a normal baseline performance receive haloperidol 1.0 mg/kg p.o. to determine the "knock-out" time (blocking of "avoidance and escpe"). Monkeys having stable "knock-out" times are selected for the evaluation of test preparations as a potential cerebral insufficiency improver. The test preparations can be injected at various times before the treatment with haloperidol.

A dosage of a test preparation is considered to be active, if the administration before the treatment with haloperidol, produces a significant delay in the "knock-out" time. The test preparation is administered at different times prior to treatment with haloperidol.

In this test the minimum active dosage of 1-(p-methoxybenzyl)-2-pyrrolidinone was 1 mg/kg i.p.

The acute toxicities of the compounds of formula I in mice are as follows:

| $R_1$ | $LD_{50}$ |
|---|---|
| p-Methoxybenzyl | 2000–4000 mg/kg p.o. |
| p-Fluorobenzyl | 1000–2000 mg/kg p.o. |
| o-Methoxybenzoyl | 5000 mg/kg p.o. |
| m-Methoybenzyl | 1250–2500 mg/kg p.o. |

The compounds of formula I are useful as agents for the control or prevention of cerebral insufficiency and in the improvement of intellectual capacity, for example in cases of cerebral seizure, in geriatry, (e.g. for improvement of geriatric cognitive processes) in alcoholism etc. The dosage can vary within wide limits and is, of course, determined by individual requirements in each particular case. Generally, an orally administered daily dosage of about 10 mg to 2500 mg of a compound of formula I is suitable, although the upper limit can be exceeded if necessary.

Qualitatively, the compounds of formula I have a similar or better action than piracetam or HYDERGINE, which are known for their therapeutic use.

The compounds of formula I can be used as medicaments, for instance, in the form of pharmaceutical compositions which contain them in association with a pharmaceutically acceptable, inert organic or inorganic carrier material. The pharmaceutical compositions can be administered orally, for example in the form of tablets, varnished tablets, dragees, hard gelatin capsules, soft gelatin capsules, solutions, emulsions or suspensions. Alternatively, the compositions can be administered rectally, for example in the form of suppositories, or parenterally, for example in the form of injectable solutions.

Suitable inert carrier materials include by way of example, the following: maize starch or derivatives thereof, talc, and stearic acid or salts thereof for tablets, dragees and hard gelatin capsules; vegetable oils, waxes, fats, semi-solid and liquid polyols and the like for soft gelatin capsules; water, polyols, saccharose, invert sugar, glucose and the like for solutions and syrups; water, alcohols, polyols, glycerine, vegetable oils and the like, for injectable solutions; and natural or hardened oils, waxes, fats, semi-liquid or liquid polyols and the like for suppositories.

The pharmaceutical compositions may also contain adjuvants such as preserving agents, solubilizing agents, stabilizing agents, wetting agents, emulsifying agents, sweetening agents, coloring agents, flavoring agents, salts for varying the osmotic pressure, buffers, coating agents or antioxidants.

The following Examples illustrate typical pharmaceutical compositions of the invention containing 1-(p-methoxybenzyl)-2-pyrrolidinone as the active substance.

EXAMPLE 1

| Soft Gelatin Capsule | |
|---|---|
| | Per capsule |
| 1-(p-methoxybenzyl)-2-pyrrolidinone | 40 mg |
| Triglyceride mixture fractionated from coconut oil | 150 mg |
| Total capsule content | 190 mg |

EXAMPLE 2

| Injectable solution | | |
|---|---|---|
| 1-(p-methoxybenzyl)-2-pyrrolidinone | | 20.0 mg |
| Polyethyleneglycol 400 | | 0.3 ml |
| Sodium chloride | | 2.7 mg |
| Water for injection | to | 1 ml. |

EXAMPLE 3

| Liquid composition (emulsion) for oral administration | |
|---|---|
| | Per 100 ml of emulsion |
| 1-(p-methoxybenzy)-2-pyrrolidinone | 0.8 g |
| Neutral oil | q.s. |
| Sodium carboxymethylcellulose | 0.6 g |
| Polyoxyethylene stearate | q.s. |
| Glycerine (pure) | 0.2–2.0 g |
| Preserving agent | q.s. |
| Flavor adjuster | q.s. |
| Water (deionized or distilled) | to 100 ml |

EXAMPLE 4

| Rectal Suppository | |
|---|---|
| | Per Suppository |
| 1-(p-methoxybenzyl)-2-pyrrolidinone | 40 mg |
| Suppository base | to 2 g |

The foregoing pharmaceutical compositions were prepared using methods known in the art.

We claim:

1. A method of counteracting cerebral insufficiency and improving intellectual capacity in a mammal comprising administering to said mammal, in an amount sufficient to counteract cerebral insufficiency and improve intellectual capacity, a compound of the formula

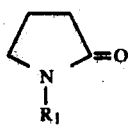

wherein R1 is o-methoxybenzoyl, m-methoxybenzyl, p-methoxybenzyl or p-fluorobenzyl, and a pharmaceutically acceptable inert carrier material.

2. A method in accordance with claim 1, wherein said compound is 1-(p-methoxybenzyl)-2-pyrrolidinone.

* * * * *

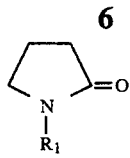

wherein R1 is o-methoxybenzoyl, m-methoxybenzyl, p-methoxybenzyl or p-fluorobenzyl, and a pharmaceutically acceptable inert carrier material.

2. A method in accordance with claim 1, wherein said compound is 1-(p-methoxybenzyl)-2-pyrrolidinone.

* * * * *